United States Patent
Lasheras et al.

(10) Patent No.: US 6,224,624 B1
(45) Date of Patent: May 1, 2001

(54) SELECTIVE ORGAN COOLING APPARATUS AND METHOD

(75) Inventors: Juan C. Lasheras, La Jolla; Randell L. Werneth, San Diego; John D. Dobak, III, La Jolla, all of CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

(21) Appl. No.: 09/291,824

(22) Filed: Apr. 14, 1999

Related U.S. Application Data

(63) Continuation-in-part of application No. 09/215,038, filed on Dec. 16, 1998, which is a continuation-in-part of application No. 09/103,342, filed on Jun. 23, 1998, now Pat. No. 6,096,068, and a continuation of application No. 09/047,012, filed on Mar. 24, 1998, now Pat. No. 5,957,963, and a continuation of application No. 09/052,545, filed on Mar. 31, 1998.

(51) Int. Cl.[7] ...................................................... A61F 7/00
(52) U.S. Cl. .......................... 607/105; 607/106; 128/898; 606/20; 606/27
(58) Field of Search .............................. 607/96, 104, 105, 607/106, 113; 606/27, 28, 23, 20, 21, 22, 31, 191, 192, 194; 604/96, 97, 113; 128/898

(56) References Cited

U.S. PATENT DOCUMENTS

| | | |
|---|---|---|
| 2,308,484 | 1/1943 | Auzin et al. ............................. 18/58 |
| 2,374,609 | 4/1945 | MacCollum . |
| 2,615,686 | 10/1952 | Davidson . |
| 2,672,032 | 3/1954 | Towse . |
| 2,913,009 | 11/1959 | Kuthe ..................................... 138/38 |
| 3,298,371 | 1/1967 | Lee . |
| 3,425,419 | 2/1969 | Dato . |

(List continued on next page.)

FOREIGN PATENT DOCUMENTS

| | | |
|---|---|---|
| 655225 | 9/1994 | (EP) . |
| 2447406 | 11/1981 | (FR) . |
| PCT/WO91/ 05528 | 5/1991 | (WO) . |
| WO 95/01814 | 1/1993 | (WO) . |
| WO 93/04727 | 3/1993 | (WO) . |
| 96/40347 | 12/1996 | (WO) . |

(List continued on next page.)

OTHER PUBLICATIONS

Ambrus; The Biphasic Nature and Temperature Dependence of the Activation of Human Plasminogen by Urokinase; May 1979; pp. 339–347; Research Communications in Chemical Pathology and Pharmacology, vol. 24, No. 2.

Bigelo; Hypothermia, Its Possible Role in Cardiac Surgery; Nov. 1959; pp. 849–866; Annals of Surgery, vol. 132, No. 5.

Cheatle; Cryostripping the Long and Short Saphenous Veins; Jan. 1993; one page; Br. J. Surg., vol. 80.

Dexter; Blood Warms as It Flows Retrograde from a Femoral Cannulation Site to the Carotic Artery During Cardiopulmonary Bypass; Nov. 1994; pp. 393–397; Perfusion, vol. 9, No. 6.

(List continued on next page.)

*Primary Examiner*—Lee Cohen
*Assistant Examiner*—R. Kearney
(74) *Attorney, Agent, or Firm*—Lyon & Lyon LLP

(57) ABSTRACT

The present invention involves a selective organ heat transfer device having a flexible coaxial catheter capable of insertion into a selected feeding artery in the vascular system of a patient. A heat transfer element is attached to a distal portion of the catheter as well as a turbulence-enhancing element which is adapted to enhance turbulent blood flow along the heat transfer element. The heat transfer element may include the turbulence-enhancing element and/or a turbulence-enhancing element may be located proximal of the heat transfer element.

20 Claims, 11 Drawing Sheets

U.S. PATENT DOCUMENTS

| | | |
|---|---|---|
| 3,504,674 | 4/1970 | Swenson et al. . |
| 3,865,116 | 2/1975 | Brooks . |
| 3,888,259 | 6/1975 | Miley . |
| 3,971,383 | 7/1976 | van Gerven . |
| 4,038,519 | 7/1977 | Foucras . |
| 4,153,048 | 5/1979 | Magrini . |
| 4,190,033 | 2/1980 | Foti . |
| 4,231,425 | 11/1980 | Engstrom . |
| 4,275,734 | 6/1981 | Mitchiner . |
| 4,298,006 | 11/1981 | Parks . |
| 4,318,722 | 3/1982 | Altman . |
| 4,427,009 | 1/1984 | Wells et al. . |
| 4,445,500 | 5/1984 | Osterholm . |
| 4,483,341 | 11/1984 | Witteles . |
| 4,502,286 | 3/1985 | Okada et al. . |
| 4,569,355 | 2/1986 | Bitterly . |
| 4,581,017 | 4/1986 | Sahota . |
| 4,655,746 | 4/1987 | Daniels et al. . |
| 4,672,962 | 6/1987 | Hershenson . |
| 4,748,979 | 6/1988 | Hershenson . |
| 4,750,493 | 6/1988 | Brader . |
| 4,762,129 | 8/1988 | Bonzel . |
| 4,762,130 | 8/1988 | Fogarty et al. . |
| 4,820,349 | 4/1989 | Saab . |
| 4,860,744 | 8/1989 | Johnson et al. . |
| 4,883,455 | 11/1989 | Leonard . |
| 4,894,164 | 1/1990 | Polaschegg . |
| 4,904,237 | 2/1990 | Janese . |
| 4,920,963 | 5/1990 | Brader . |
| 4,964,409 | 10/1990 | Tremulis . |
| 5,002,531 | 3/1991 | Bonzel . |
| 5,014,695 | 5/1991 | Benak et al. . |
| 5,018,521 | 5/1991 | Campbell . |
| 5,019,075 | 5/1991 | Spears et al. . |
| 5,041,089 | 8/1991 | Mueller et al. . |
| 5,078,713 | 1/1992 | Varney . |
| 5,092,841 | 3/1992 | Spears . |
| 5,106,360 | 4/1992 | Ishiwara et al. . |
| 5,108,390 | 4/1992 | Potocky et al. . |
| 5,110,721 | 5/1992 | Anaise et al. . |
| 5,117,822 | 6/1992 | Laghi . |
| 5,147,355 | 9/1992 | Friedman et al. . |
| 5,149,321 | 9/1992 | Klatz et al. . |
| 5,150,706 | 9/1992 | Cox et al. . |
| 5,151,100 | 9/1992 | Abele et al. . |
| 5,190,539 | 3/1993 | Fletcher et al. . |
| 5,191,883 | 3/1993 | Lennox et al. . |
| 5,196,024 | 3/1993 | Barath . |
| 5,211,631 | 5/1993 | Sheaff . |
| 5,234,405 | 8/1993 | Klatz et al. . |
| 5,246,421 | 9/1993 | Saab . |
| 5,248,312 | 9/1993 | Langberg . |
| 5,250,070 | 10/1993 | Parodi . |
| 5,257,977 | 11/1993 | Eshel . |
| 5,264,260 | 11/1993 | Saab . |
| 5,269,369 | 12/1993 | Faghri . |
| 5,269,749 | 12/1993 | Koturov . |
| 5,269,758 | 12/1993 | Taheri . |
| 5,281,213 | 1/1994 | Milder et al. . |
| 5,281,215 | 1/1994 | Milder . |
| 5,306,261 | 4/1994 | Alliger et al. . |
| 5,310,440 | 5/1994 | Zingher . |
| 5,334,193 | 8/1994 | Nardella . |
| 5,342,301 | 8/1994 | Saab . |
| 5,342,621 | 8/1994 | Eury . |
| 5,344,436 | 9/1994 | Fontenot et al. . |
| 5,358,486 | 10/1994 | Saab . |
| 5,365,750 | 11/1994 | Greenthal . |
| 5,368,591 | 11/1994 | Lennox et al. . |
| 5,383,918 | 1/1995 | Panetta . |
| 5,395,314 | 3/1995 | Klatz et al. . |
| 5,395,331 | 3/1995 | O'Neill et al. . |
| 5,403,281 | 4/1995 | O'Neill et al. . |
| 5,417,686 | 5/1995 | Peterson et al. . |
| 5,423,745 | 6/1995 | Todd et al. . |
| 5,423,807 | 6/1995 | Milder . |
| 5,433,740 | 7/1995 | Yamaguchi . |
| 5,437,673 | 8/1995 | Baust et al. . |
| 5,462,521 | 10/1995 | Brucker et al. . |
| 5,486,204 | 1/1996 | Clifton . |
| 5,486,208 | 1/1996 | Ginsburg ................................ 607/106 |
| 5,531,776 | 7/1996 | Ward et al. . |
| 5,558,644 | 9/1996 | Boyd et al. . |
| 5,569,165 | 10/1996 | Saab . |
| 5,573,532 | 11/1996 | Chang et al. . |
| 5,584,804 | 12/1996 | Klatz et al. . |
| 5,588,438 | 12/1996 | McKown et al. . |
| 5,591,162 | 1/1997 | Fletcher et al. . |
| 5,620,480 | 4/1997 | Rudie . |
| 5,624,392 | 4/1997 | Saab . |
| 5,643,197 | 7/1997 | Brucker et al. . |
| 5,647,051 | 7/1997 | Neer . |
| 5,676,693 | 10/1997 | LaFontaine . |
| 5,709,654 | 1/1998 | Klatz . |
| 5,713,941 | 2/1998 | Robins et al. . |
| 5,716,386 | 2/1998 | Ward et al. . |
| 5,735,809 | 4/1998 | Gorsuch ................................ 604/4 |
| 5,787,878 | 8/1998 | Bleam . |
| 5,800,480 | 9/1998 | Augustine et al. . |
| 5,807,391 | 9/1998 | Wijkamp . |
| 5,824,030 | 10/1998 | Yang et al. . |
| 5,827,222 | 10/1998 | Klatz et al. . |
| 5,827,237 | 10/1998 | Macoviak et al. . |
| 5,833,671 | 11/1998 | Macoviak et al. . |
| 5,837,003 | 11/1998 | Ginsburg . |
| 5,871,526 | 2/1999 | Gibbs et al. . |
| 5,873,835 | 2/1999 | Hastings et al. . |
| 5,879,329 | 3/1999 | Ginsburg . |
| 5,899,899 | 5/1999 | Arless et al. . |
| 5,902,268 | 5/1999 | Saab . |
| 5,913,885 | 6/1999 | Klatz et al. . |
| 5,913,886 | 6/1999 | Soloman . |
| 5,916,242 | 6/1999 | Schwartz . |
| 5,957,963 | 9/1999 | Dobak, III . |
| 5,989,238 | 11/1999 | Ginsburg . |
| 6,019,783 | 2/2000 | Phillips et al. . |
| 6,033,383 | 3/2000 | Ginsburg . |
| 6,042,559 | 3/2000 | Dobak, III . |
| 6,051,019 | 4/2000 | Dobak, III . |
| 6,096,068 | 8/2000 | Dobak, III et al. . |
| 6,110,168 | 8/2000 | Ginsburg . |

FOREIGN PATENT DOCUMENTS

| | | |
|---|---|---|
| WO 97/01374 | 1/1997 | (WO) . |
| WO 97/25011 | 7/1997 | (WO) . |
| PCT/WO98/26831 | 6/1998 | (WO) . |
| WO 98/31312 | 7/1998 | (WO) . |
| WO 99/66970 | 12/1999 | (WO) . |
| WO 99/66971 | 12/1999 | (WO) . |
| WO 00/09054 | 2/2000 | (WO) ................................ A61F/7/12 |
| WO 00/10494 | 3/2000 | (WO) ................................ A61F/7/00 |
| WO 00/38601 | 7/2000 | (WO) . |
| WO 00/47145 | 8/2000 | (WO) . |
| WO 00/47415 | 8/2000 | (WO) . |
| WO 00/48670 | 8/2000 | (WO) . |

OTHER PUBLICATIONS

Gillinov; Superior Cerebral Protection with Profound Hypothermia During Circulatory Arrest; Nov. 1992; pp. 1432–1439; Ann. Thorac. Surg., vol. 55.

Higazi; The Effect of Ultrasonic Irradiation and Temperature on Fibrinolytic Activity in Vitro; Aug. 1992; p. 251–253; Thrombosis Research, vol. 69, No. 2.

Imamaki; Retrograde Cerebral Perfusion with Hypothermic Blood Provides Efficient Protection of the Brain; Jul. 1995; pp. 325–333; Journal of Cardiac Surgery, vol. 10, No. 4, Part 1.

Jolin; Management of a Giant Intracranial Aneurysm Using Surface–Heparinized Extracorporeal Circulaiton and Controlled Deep Hypothermic Low Flow Perfusion; Aug. 1992; pp. 756–760; Acta Anaesthesiologica Scandinavia.

Kimoto; Open Heart Surgery under Direct Vision with the Aid of Brain–Cooling by Irrigation; Jul. 1955; pp. 592–603; Surgery, vol. 39, No. 4.

Marekovic, Z.; Abstract of Renal Hypothermia in Situ by Venous Passages: Experimental Work on Dogs; 1980; Eur Urol 6(2); 1 page.

Meden; Effect of Hypothermia and Delayed Thrombolysis in a Rat Embolic Stroke Model; Dec. 1993; pp. 91–98; Acta Neurologica Scandinavica.

Meden; The Influence of Body Temperature on Infarct Volume and Thrombolytic Therapy in a Rat Embolic Stroke Model; Feb. 1994; pp. 131–138; Brain Research, vol. 647.

Milleret, Rene; La cryo–chirurgie danes les varices des mimbres inferieurs; Angiologie; Supplement au no. 110.

Milleret; Abstract of Cryosclerosis of the Saphenous Veins in Varicose Reflux in the Obese and Elderly; 10.1981; one page; Phlebologie, vol. 34, No. 4.

Parkins; Brain Cooling in the Prevention of Brain Damage During Periods of Circulatory Occlusion in Dogs; Apr. 1954; pp. 284–289; Annals of Surgery, vol. 140, No. 3.

Piepgras; Rapid Active Internal Core Cooling for Induction of Moderate Hypothermia in Head Injury by Use of an Extracorporeal Heat Exchanger; Feb. 1998; pp. 311–318; Neurosurgery, vol. 42, No. 2.

Rijken; Plasminogen Activation at Low Temperatures in Plasma Samples Containing Therapeutic Concentrations of Tissue–Type Plasminogen Activator or Thrombolytic Agents; Oct. 1989; pp. 47–52; place of publication unknown.

Schwartz; Selective Cerebral Hypothermia by Means of Transfemoral Internal Carotid Artery Catheterization; May 1996; pp. 571–572; Radiology,vol. 201, No. 2.

Steen; The Detrimental Effects of Prolonged Hypothermia and Rewarming in the Dog; Aug. 1979 ;pp. 224–230; Anesthesiology, vol. 52, No. 3.

Vandam; Hypothermia; Sep. 1959; pp. 546–553; The New England Journal of Medicine.

White; Cerebral Hypothermia and Circulatory Arrest; Jul. 1978; pp. 450–458; Mayo Clinic Proceedings, vol. 53.

Yenari; Thrombolysis with Tissue Plasminogen Activator (TPA) is Temperature Dependent; Jul. 1994; pp. 475–481; Thrombosis Research, vol. 77, No. 5.

Yoshihara; Changes in Coagulation and Fibrinolysis Occurring in Dogs during Hypothermia; Aug. 1984; pp. 503–512; Thrombosis Research, vol. 37, No. 4.

Zarins; Circulation in Profound Hypothermia; Nov. 1972; pp. 97–104; Journal of Surgical Research, vol. 14, No. 2.

Jansen et al., "Near Continuous Cardiac Output by Thermodilution", Journal of Clinical Monitoring, vol. 13, No. 4, pp. 233–239, Jul., 1997.

Schwartz et al., "Cerebral Blood Flow During Low–Flow Hypothermic Cardiopulmonary Bypass in Baboons", Anesthesiology, vol. 81, No. 4, pp. 959–964, Oct., 1994.

Schwartz et al., "Isolated Cerebral Hypothermia by Single Carotid Artery Perfusion of Extracorporeally Cooled Blood in Baboons", Neurosurgery, vol. 39, No. 3, pp. 577–582, Sep., 1996.

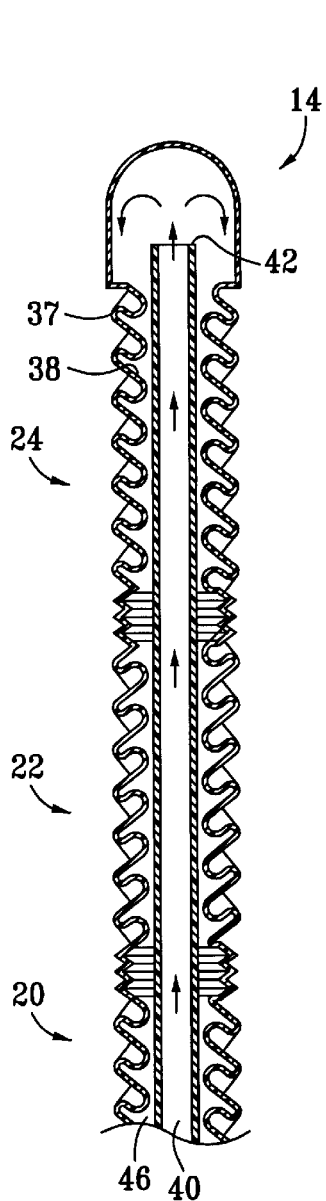
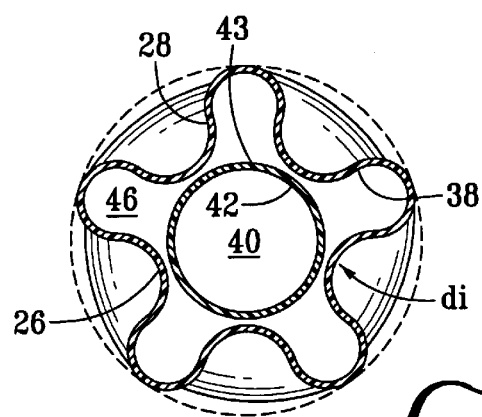
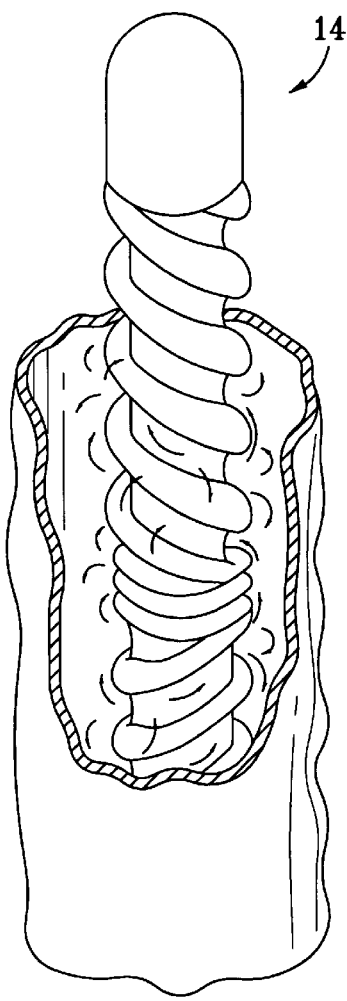
fig. 5
fig. 6
fig. 7

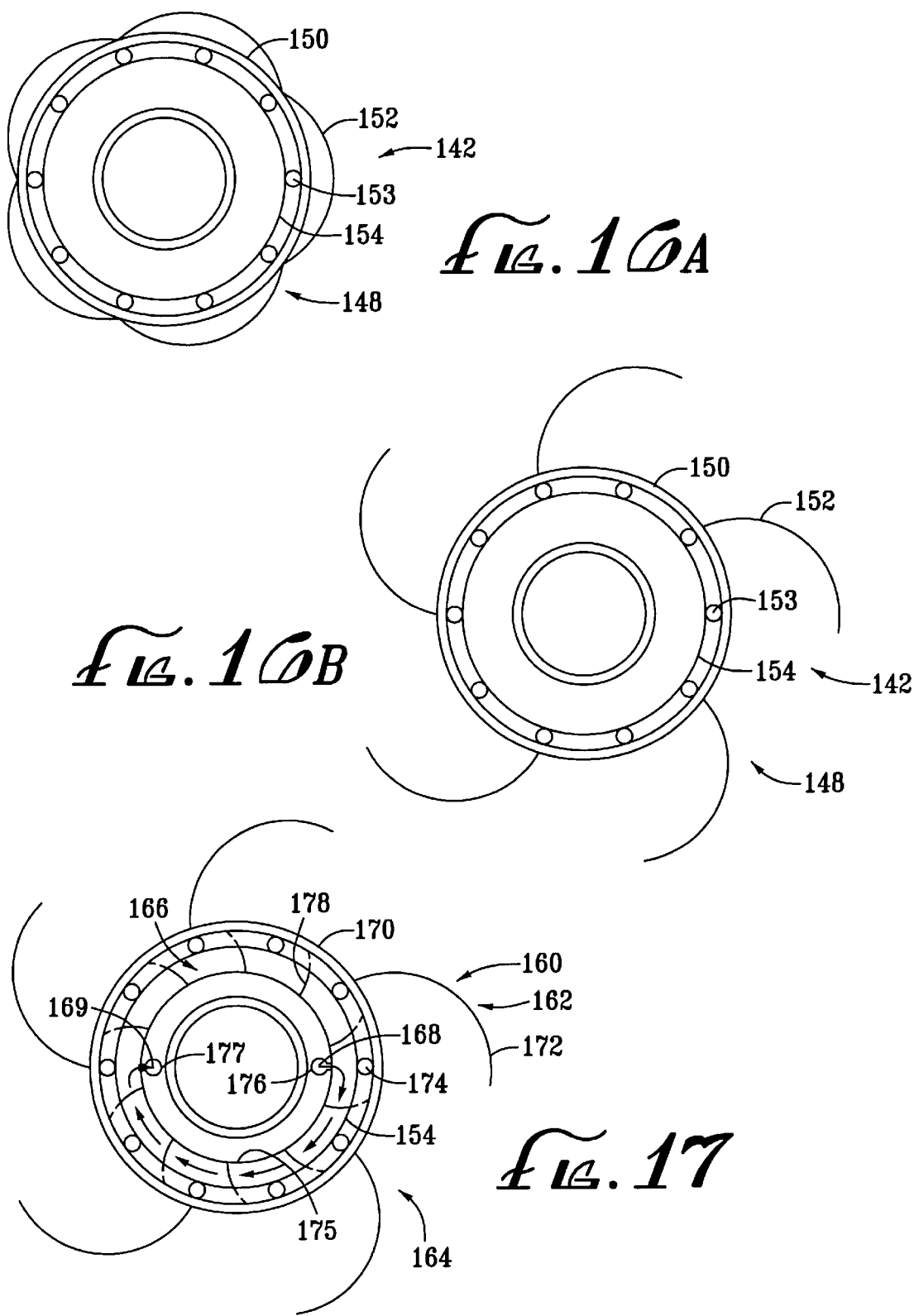

SELECTIVE ORGAN COOLING APPARATUS AND METHOD

RELATED APPLICATIONS

This is a continuation-in-part of U.S. patent application Ser. No. 09/215,038, filed on Dec. 16, 1998, and entitled "Inflatable Catheter for Selective Organ Heating and Cooling and Method of Using the Same," which is a continuation-in-part of: U.S. patent application Ser. No. 09/103,342, filed on Jun. 23, 1998 U.S. Pat. No. 6,096,068, and entitled "Selective Organ Cooling Catheter and Method of Using the Same"; and a continuation of U.S. patent application Ser. No. 09/047,012, filed on Mar. 24, 1998, and entitled "Selective Organ Hypothermia Method and Apparatus" U.S. Pat. No. 5,957,963; and co-pending U.S. patent application Ser. No. 09/052,545, filed on Mar. 31, 1998, and entitled "Circulating Fluid Hypothermia Method and Apparatus". The disclosures of each of the above-identified applications are incorporated herein by reference.

BACKGROUND OF THE INVENTION

Field of the Invention—The present invention relates generally to the modification and control of the temperature of a selected body organ. More particularly, the invention relates to a method and intravascular apparatus for controlling organ temperature.

Background Information—Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. However, the use of total body hypothermia risks certain deleterious systematic vascular effects. For example, total body hypothermia may cause severe derangement of the cardiovascular system, including low cardiac output, elevated systematic resistance, and ventricular fibrillation. Other side effects include renal failure, disseminated intravascular coagulation, and electrolyte disturbances. In addition to the undesirable side effects, total body hypothermia is difficult to administer.

Catheters have been developed which are inserted into the bloodstream of the patient in order to induce total body hypothermia. For example, U.S. Pat. No. 3,425,419 to Dato describes a method and apparatus of lowering and raising the temperature of the human body. The Dato patent is directed to a method of inducing moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. However, use of the Dato system implicates the negative effects of total body hypothermia described above.

Due to the problems associated with total body hypothermia, attempts have been made to provide more selective cooling. For example, cooling helmets or head gear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. Further, from a practical standpoint, cooling helmets and head gear are cumbersome and may make continued treatment of the patient difficult or impossible.

Selected organ hypothermia has been accomplished using extracorporeal perfusion, as detailed by Arthur E. Schwartz, M.D. et al., in Isolated Cerebral Hypothermia by Single Carotid Artery Perfusion of Extracorporeally Cooled Blood in Baboons, which appeared in Vol. 39, No. 3, NEUROSURGERY 577 (September, 1996). In this study, blood was continually withdrawn from baboons through the femoral artery. The blood was cooled by a water bath and then infused through a common carotid artery with its external branches occluded. Using this method, normal heart rhythm, systemic arterial blood pressure and arterial blood gas values were maintained during the hypothermia. This study showed that the brain could be selectively cooled to temperatures of 20° C. without reducing the temperature of the entire body. However, external circulation of blood is not a practical approach for treating humans because the risk of infection, need for anticoagulation, and risk of bleeding is too great. Further, this method requires cannulation of two vessels making it more cumbersome to perform, particularly in emergency settings. Moreover, percutaneous cannulation of the carotid artery is difficult and potentially fatal due to the associated arterial wall trauma. Finally, this method would be ineffective to cool other organs, such as the kidneys, because the feeding arteries cannot be directly cannulated percutaneously.

Selective organ hypothermia has also been attempted by perfusion of a cold solution such as saline or perflourocarbons. This process is commonly used to protect the heart during heart surgery and is referred to as cardioplegia. Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

SUMMARY

The present invention involves an apparatus and method for controlling the temperature of a selected organ such as the brain.

The present invention provides a system, which may be used to selectively control the temperature of a chosen organ, without inducing total body hypothermia. The apparatus, according to the invention, may include a catheter having a heat transfer element attached to a distal portion thereof. The heat transfer element allows the fluid proximate the selected organ to be cooled or heated. A turbulence-enhancing element is also attached to a distal portion of the catheter and is adapted to enhance turbulent blood flow along the heat transfer element, so as to increase the efficiency of the heat transfer.

Other advantages, features, and objects of the invention are described in the detailed description below.

BRIEF DESCRIPTION OF THE DRAWINGS

FIG. 5 is longitudinal section view of the heat transfer element of FIG. 4;

FIG. 6 is a transverse section view of the heat transfer element of FIG. 4;

FIG. 7 is a perspective view of the heat transfer element of FIG. 4 in use within a blood vessel;

FIGS. 16A, 16B are transverse section views taken along lines 16A—16A, 16B—16B of FIG. 15, with FIG. 16A illustrating the heat transfer mechanism in a low-profile position and FIG. 16B illustrating the heat transfer mechanism in an expanded position;

FIG. 17 is a cross-sectional view, similar to FIGS. 16A and 16B, of an additional embodiment of a heat transfer mechanism according to the invention;

DETAILED DESCRIPTION OF THE INVENTION

Figure 1:
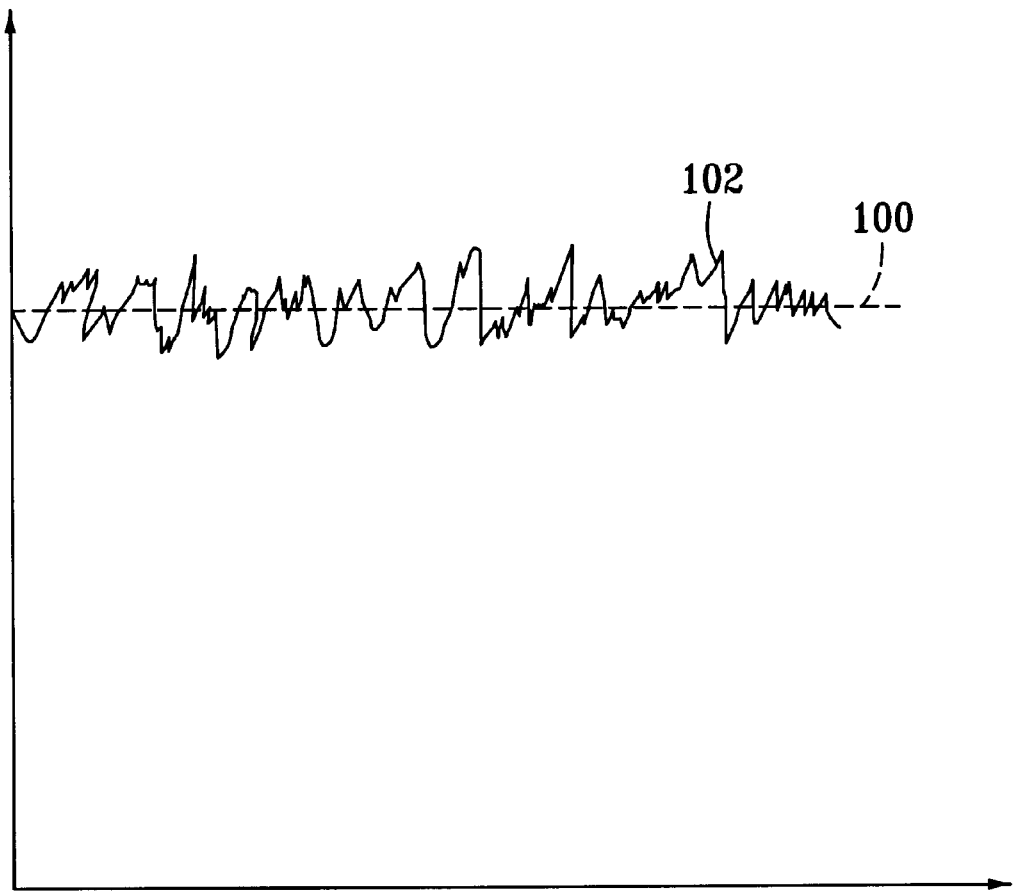
FIG. 1 is a graph illustrating the velocity of steady state turbulent flow as a function of time.

In order to intravascularly regulate the temperature of a selected organ, a heat transfer element may be placed in the feeding artery of the organ to absorb or deliver the heat from or to the blood flowing into the organ. The transfer of heat may cause either a cooling or a heating of the selected organ. The heat transfer element should be small enough to fit within the feeding artery while still allowing sufficient blood flow to reach the organ in order to avoid ischemic organ damage. The heat transfer element should also provide the necessary heat transfer rate to produce the desired cooling or heating effect within the organ. By placing the heat transfer element within the feeding artery of an organ, the temperature of an organ can be controlled without significantly effecting the remaining parts of the body. These points can be illustrated by using brain cooling as an example.

The common carotid artery supplies blood to the head and brain. The internal carotid artery branches off of the common carotid to directly supply blood to the brain. To selectively cool the brain, a heat transfer element may be placed into the common carotid artery, the internal carotid artery, or both. The internal diameter of the common carotid artery ranges from 6 to 8 mm and the length ranges from 80 to 120 mm. Thus, the heat transfer element residing in one of these arteries should not be much larger than 4 mm in diameter in order to avoid occluding the vessel.

It is advantageous that the heat transfer element be flexible in order to be placed within a small feeding artery of an organ. Feeding arteries, like the carotid artery, branch off the aorta at various levels. Subsidiary arteries continue to branch off the initial branches. For example, the internal carotid artery is a small diameter artery that branches off of the common carotid artery near the angle of the jaw. Because the heat transfer element is typically inserted into a peripheral artery, such as the femoral artery, and accesses the feeding artery by initially passing though a series of one or more of these branches, the flexibility of the heat transfer element is highly advantageous. Further, the heat transfer element is ideally constructed from a highly thermally conductive material, such as metal, in order to facilitate heat transfer. The use of a highly thermally conductive material increases the heat transfer rate for a given temperature differential between the heat transfer substance (e.g. coolant) within the heat transfer element and the blood. This facilitates the use of a higher temperature coolant within the heat transfer element, allowing safer coolants, such as water, to be used. Highly thermally conductive materials, such as metals, tend to be rigid. Therefore, the design of the heat transfer element should facilitate flexibility in an inherently inflexible material.

In order to obtain the benefits of hypothermia described above, it is desirable to reduce the temperature of the blood flowing to the brain to between 30° C. and 32° C. Given that a typical brain has a blood flow rate through each carotid artery (right and left) of approximately 250–375 cubic centimeters per minute, it is desirable for the heat transfer element to absorb 75–175 Watts of heat when placed in one of the carotid arteries, to induce the desired cooling effect. It should be noted that smaller organs may have less blood flow in the supply artery and may require less heat transfer, such as 25 Watts.

When a heat transfer element is inserted coaxially into an artery, the primary mechanism of heat transfer between the surface of the heat transfer element and the blood is forced convection. Convection relies upon the movement of fluid to transfer heat. Forced convection results when an external force causes motion within the fluid. In the case of arterial flow, the beating heart causes the motion of the blood around the heat transfer element.

The magnitude of the heat transfer rate is proportional to the surface area of the heat transfer element, the temperature differential, and the heat transfer coefficient of the heat transfer element.

As noted above, the receiving artery into which the heat transfer element is placed has a limited diameter and length. Thus, surface area of the heat transfer element must be limited to avoid significant obstruction of the artery, and to allow the heat transfer element to easily pass through the vascular system. For placement within the internal and common carotid artery, the cross sectional diameter of the heat transfer element is limited to about 4 mm, and its length is limited to approximately 10 cm.

The temperature differential can be increased, in the case of cooling, by decreasing the surface temperature of the heat transfer element. However, the minimum allowable surface temperature is limited by the characteristics of blood. Blood freezes at approximately 0° C. When the blood approaches freezing, ice emboli may form in the blood which may lodge downstream, causing serious ischemic injury. Furthermore, reducing the temperature of the blood also increases its viscosity, which results in a small decrease in the value of the convection heat transfer coefficient. In addition, increased viscosity of the blood may result in an increase in the pressure drop within the artery, thus, compromising the flow of blood to the brain. Given the above constraints, it is advantageous to limit the minimum allowable surface temperature of the heat transfer element to approximately 5° C. This results in a maximum temperature differential between the blood stream and the heat transfer element of approximately 32° C., where the patient has a normal 37° C. temperature.

The mechanisms by which the value of the convection heat transfer coefficient may be increased are complex. However, it is well known that the convection heat transfer coefficient increases with the level of turbulent kinetic energy in the fluid flow. Thus, it is advantageous to have turbulent blood flow in contact with the heat transfer element.

FIG. 1 is a graph illustrating steady state turbulent flow. The vertical axis is the velocity of the flow. The horizontal axis represents time. The average velocity of the turbulent flow is shown by a line 100. The actual instantaneous velocity of the flow is shown by a curve 102.

Figure 3A:
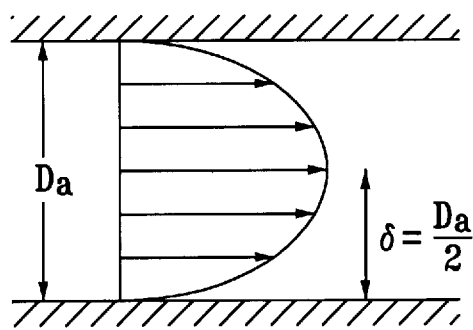
FIG. 3A is a velocity profile diagram showing a typical steady state Poiseuillean flow driven by a constant pressure gradient.

Under constant pressure conditions, the flow in a pipe is Poiseuillean. FIG. 3A is a velocity profile diagram showing a typical steady state Poiseuillean flow driven by constant pressure. The velocity of the fluid across the pipe is shown in FIG. 3A by the parabolic curve and corresponding velocity vectors. The velocity of the fluid in contact with the wall of the pipe is zero. The boundary layer is the region of the flow in contact with the pipe surface in which viscous stresses are dominant. In steady state Poiseuillean flow, the boundary layer develops until it reaches the pipe center line. For example, the boundary layer thickness in FIG. 3A is one half of the diameter of the pipe.

Under conditions of Poiseuillean flow, the Reynolds number (i.e. the ratio of inertial forces to viscous forces) can be used to characterize the level of turbulent kinetic energy. For Poiseuillean flows, Reynolds numbers must be greater than about 2300 to cause a laminar to turbulent transition. Further, when the Reynolds number is greater than about 2000, the boundary layer is receptive to "tripping". Tripping is a process by which a small perturbation in the boundary layer can create turbulent conditions. The receptivity of a boundary layer to "tripping" is proportional to the Reynolds number and is nearly zero for Reynolds numbers less than 2000.

Figure 2A:
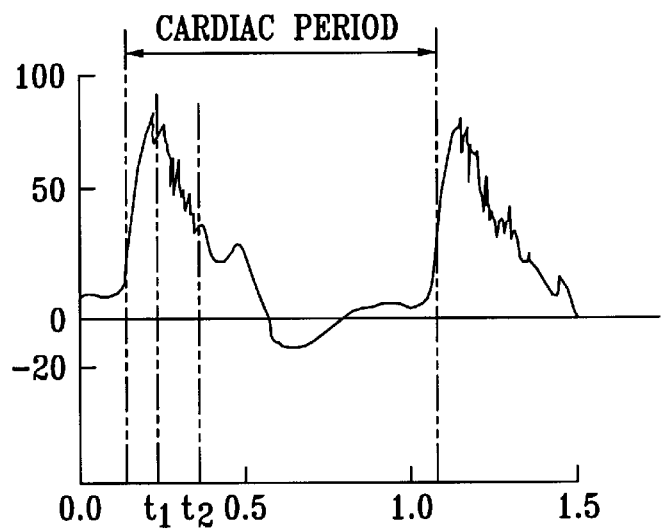
FIG. 2A is a graph showing the velocity of the blood flow within an artery as a function of time.

Blood flow in arteries is induced by the beating heart and is therefore pulsatile, complicating the fluid mechanics analysis. FIG. 2A is a graph showing the velocity of the blood flow within an artery as a function of time. The beating heart provides pulsatile flow with an approximate period of 0.5 to 1 second. This is known as the period of the cardiac cycle. The horizontal axis in FIG. 2A represents time in seconds and the vertical axis represents the average velocity of blood in centimeters per second. Although very high velocities are reached at the peak of the pulse, the high velocity occurs for only a small portion of the cycle. In fact, as shown in FIG. 2A, the velocity of the blood reaches zero in the carotid artery at the end of a pulse and temporarily reverses.

Figure 3B:
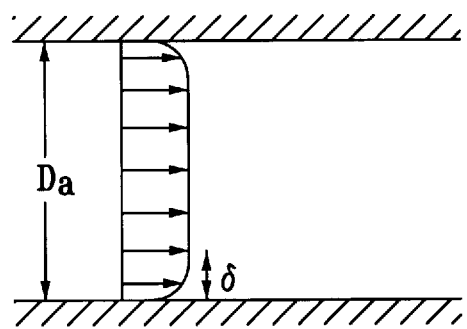
FIG. 3B is a velocity profile diagram showing blood flow velocity within an artery, averaged over the duration of the cardiac pulse.

Because of the relatively short duration of the cardiac pulse, the blood flow in the arteries does not develop into classic Poiseuillean flow. FIG. 3B is a velocity profile diagram showing blood flow velocity within an artery averaged over the cardiac pulse. The majority of the flow within the artery has the same velocity. The boundary layer where the flow velocity decays from the free stream value to zero is very thin, typically $\frac{1}{6}$ to $\frac{1}{20}$ of the diameter of the artery, as opposed to one half of the diameter of the artery in the Poiseuillean flow condition.

As noted above, if the flow in the artery were steady rather than pulsatile, the transition from laminar to turbulent flow would occur when the value of the Reynolds number exceeds about 2000. However, in the pulsatile arterial flow, the value of the Reynolds number varies during the cardiac cycle, just as the flow velocity varies. In pulsatile flows, due to the enhanced stability associated with the acceleration of the free stream flow, the critical value of the Reynolds number at which the unstable modes of motion grow into turbulence is found to be much higher, perhaps as high as 9000.

The blood flow in the arteries of interest remains laminar over more than 80% of the cardiac cycle. Referring again to FIG. 2A, the blood flow is turbulent from approximately time $t_1$ until time $t_2$ during a small portion of the descending systolic flow, which is less than 20% of the period of the cardiac cycle. If a heat transfer element is placed inside the artery, heat transfer will be facilitated during this short interval. However, to transfer the necessary heat to cool the brain, turbulent kinetic energy should be produced and sustained throughout the entire period of the cardiac cycle.

Figure 3C:
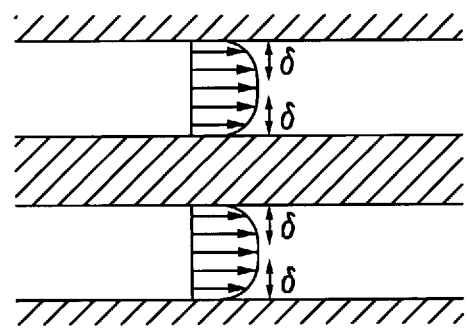
FIG. 3C is a velocity profile diagram showing blood flow velocity within an artery, averaged over the duration of the cardiac pulse, after insertion of a smooth heat transfer element within the artery.

A thin boundary layer has been shown to form during the cardiac cycle. This boundary layer will form over the surface of a smooth heat transfer element. FIG. 3C is a velocity profile diagram showing blood flow velocity within an artery, averaged over the cardiac pulse, after insertion of a smooth heat transfer element within the artery. In FIG. 3C, the diameter of the heat transfer element is about one half of the diameter of the artery. Boundary layers develop adjacent to the heat transfer element as well as next to the walls of the artery. Each of these boundary layers has approximately the same thickness as the boundary layer which would have developed at the wall of the artery in the absence of the heat transfer element. The free stream flow region is developed in an annular ring around the heat transfer element.

One way to increase the heat transfer rate is to create a turbulent boundary layer on the heat transfer element surface. However, turbulence in the very thin boundary layer will not produce sufficient kinetic energy to produce the necessary heat transfer rate. Therefore, to induce sufficient turbulent kinetic energy to increase the heat transfer rate sufficiently to cool the brain, a stirring mechanism, which abruptly changes the direction of velocity vectors, may be utilized. This can create high levels of turbulence intensity in the free stream, thereby sufficiently increasing the heat transfer rate.

Figure 2B:
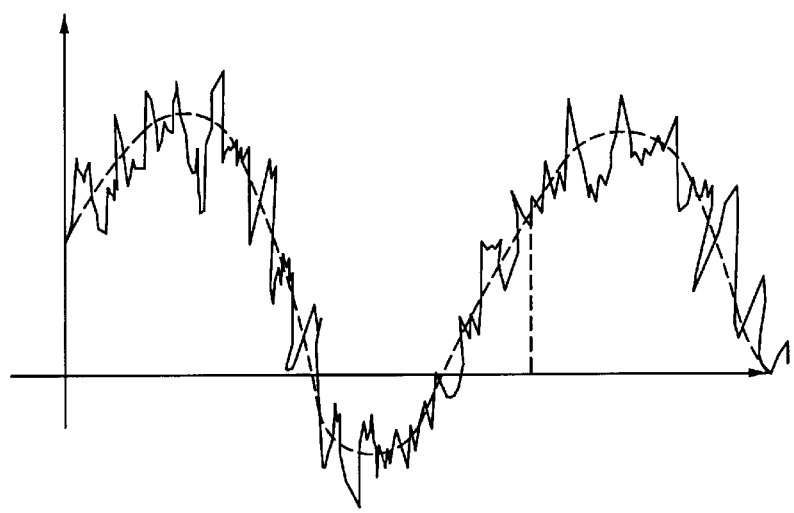
FIG. 2B is a graph illustrating the velocity of steady state turbulent flow under pulsatile conditions as a function of time, similar to arterial blood flow.

This turbulence intensity should ideally be sustained for a significant portion of the cardiac cycle. Further, turbulent kinetic energy should ideally be created throughout the free stream and not just in the boundary layer. FIG. 2B is a graph illustrating the velocity of continually turbulent flow under pulsatile conditions as a function of time, which would result in optimal heat transfer in arterial blood flow. Turbulent velocity fluctuations are seen throughout the cycle as opposed to the short interval of fluctuations seen in FIG. 2A between time $t_1$ and time $t_2$. These velocity fluctuations are found within the free stream. The turbulence intensity shown in FIG. 2B is at least 0.05. In other words, the instantaneous velocity fluctuations deviate from the mean velocity by at least 5%. Although, ideally, turbulence is created throughout the entire period of the cardiac cycle, the benefits of turbulence are obtained if the turbulence is sustained for 75%, 50% or even as low as 30% or 20% of the cardiac cycle.

Figure 2C:
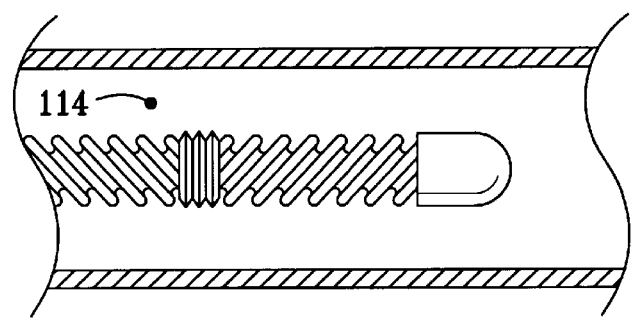
FIG. 2C is an elevation view of a turbulence inducing heat transfer element within an artery.

To create the desired level of turbulence intensity in the blood free stream during the whole cardiac cycle, one embodiment of the invention uses a modular design. This design creates helical blood flow and produces a high level of turbulence in the free stream by periodically forcing abrupt changes in the direction of the helical blood flow. FIG. 2C is a perspective view of such a turbulence inducing heat transfer element within an artery. Turbulent flow would be found at point 114, in the free stream area The abrupt changes in flow direction are achieved through the use of a series of two or more heat transfer segments, each comprised of one or more helical ridges. To affect the free stream, the depth of the helical ridge is larger than the thickness of the boundary layer which would develop if the heat transfer element had a smooth cylindrical surface.

The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry.

Figure 4:
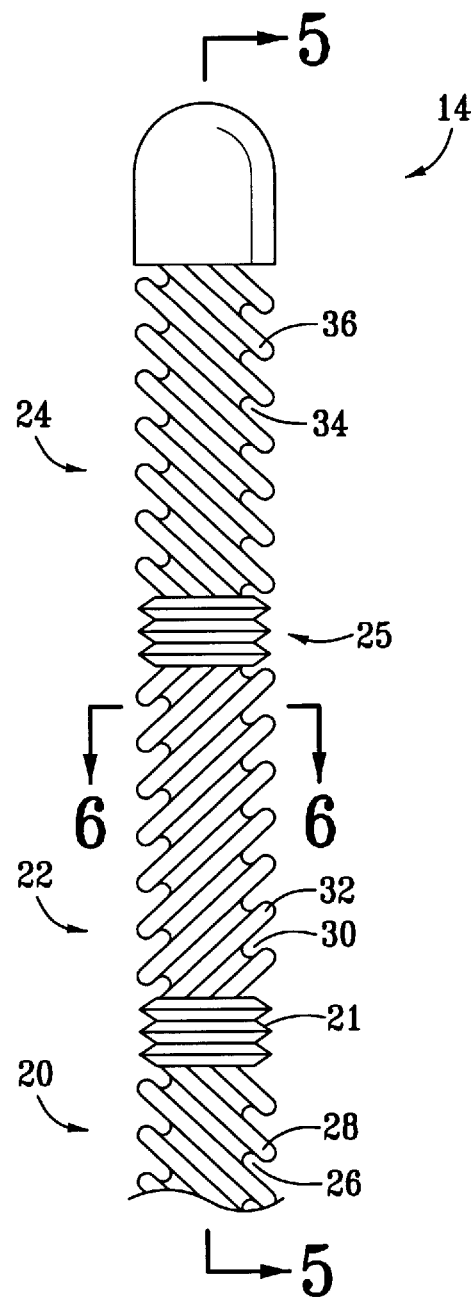
FIG. 4 is an elevation view of one embodiment of a heat transfer element according to the invention.

FIG. 4 is an elevation view of one embodiment of a heat transfer element 14 according to the present invention. The heat transfer element 14 is comprised of a series of elongated, articulated heat transfer segments 20, 22, 24 and bellows 21 and 25. Three such segments are shown in this embodiment, but two or more such segments could be used without departing from the spirit of the invention. As seen in FIG. 4, a first elongated heat transfer segment 20 is located at the proximal end of the heat transfer element 14. A turbulence-inducing exterior surface of the segment 20 comprises four parallel helical ridges 28 with four parallel helical grooves 26 therebetween. One, two, three, or more parallel helical ridges 28 could also be used and are within the scope of the present invention. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first bellows section 21, which provides flexibility and compressibility. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second bellows section 25. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20,22,24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28,32,36 also allow the heat transfer element 14 to maintain a relatively atraumatic profile, thereby minimizing the possibility of damage to the blood vessel wall. A heat transfer element according to the present invention may be comprised of two, three, or more heat transfer segments.

The bellows sections 21,25 are formed from seamless and nonporous materials, such as metal, and therefore are impermeable to gas, which can be particularly important, depending on the type of working fluid which is cycled through the heat transfer element 14. The structure of the bellows sections 21,25 allows them to bend, extend and compress, which increases the flexibility of the heat transfer element 14 so that it is more readily able to navigate through blood vessels. The bellows sections 21,25 also provide for axial compression of the heat transfer element 14, which can limit the trauma when the distal end of the heat transfer element 14 abuts a blood vessel wall. The bellows sections 21,25 are also able to tolerate cryogenic temperatures without a loss of performance.

The exterior surfaces of the heat transfer element 14 can be made from metal, and may comprise very high thermally conductive material such as nickel, thereby, facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature for a disposable medical device.

Because the heat transfer element 14 may dwell within the blood vessel for extended periods of time, such as 24–48 hours or even longer, it may be desirable to treat the surfaces of the heat transfer element 14 to avoid clot formation. In particular, one may wish to treat the bellows sections 21,25 because stagnation of the blood flow may occur in the convolutions, thus, allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and, thus, prevent adherence of clotting factors to the surface.

FIG. 5 is a longitudinal sectional view of the heat transfer element 14 of the invention, taken along line 5—5 in FIG. 4. An inner tube 40 creates an inner coaxial lumen 40 and an outer coaxial lumen 46 within the heat transfer element 14. Once the heat transfer element 14 is in place in the blood vessel, a working fluid such as saline or other aqueous solution may be circulated through the heat transfer element 14. Fluid flows from a working fluid chiller and pump, up a supply catheter and into the inner coaxial lumen 40. At the distal end of the heat transfer element 14, the working fluid exits the inner coaxial lumen 40 and enters the outer lumen 46. As the working fluid flows through the outer lumen 46, heat is transferred from the working fluid to the exterior surface 37 of the heat transfer element 14. Because the heat transfer element 14 is constructed from highly conductive material, the temperature of its exterior surface 37 may reach very close to the temperature of the working fluid. The tube 42 may be formed as an insulating divider, to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or some other polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 is particularly important when using water, saline or some other fluid which remains a liquid, as the coolant. Other coolants such as freon undergo nucleate boiling and create turbulence through a different mechanism. Saline is a safe coolant because it is non-toxic, and leakage of saline does not result in a gas embolism, which could occur with the use of boiling refrigerants. Since turbulence in the coolant is enhanced by the shape of the interior surface 38 of the heat transfer element 14, the coolant can be delivered to the heat transfer element 14 at a warmer temperature, and still achieve the necessary heat transfer rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28,32,36, the pressure of the working fluid may be as low as 5 atmospheres, 3 atmospheres, 2 atmospheres or even less than 1 atmosphere.

FIG. 6 is a transverse sectional view of the heat transfer element 14 of the invention, taken along the line 6—6 in FIG. 4. In FIG. 6, the coaxial construction of the heat transfer element 14 is clearly shown. The inner coaxial lumen 40 is defined by the insulating coaxial tube 42. The outer lumen 46 is defined by the exterior surface of the insulating coaxial tube 42 and the interior surface 38 of the heat transfer element 14. In addition, the helical ridges 28 and helical grooves 26 may be seen in FIG. 6. As noted above, in the preferred embodiment, the depth of the grooves, $d_i$, is greater than the boundary layer thickness which would have developed if a cylindrical heat transfer element were introduced. For example, in a heat transfer element 14 with a 4 mm outer diameter, the depth of the grooves, $d_i$, may be approximately equal to 1 mm if designed for use in the carotid artery. Although FIG. 6 shows four ridges and four grooves, the number of ridges and grooves may vary. Thus, heat transfer elements with 1, 2, 3, 4, 5, 6, 7, 8 or more ridges are specifically contemplated.

FIG. 7 is a perspective view of the heat transfer element 14 in use within a blood vessel. Beginning from the proximal end of the heat transfer element (not shown in FIG. 7), as the blood moves forward during the systolic pulse, the first helical heat transfer segment 20 induces a counterclockwise rotational inertia to the blood. As the blood reaches the second segment 22, the rotational direction of the inertia is reversed, causing turbulence within the blood. Further, as the blood reaches the third segment 24, the rotational direction of the inertia is again reversed. The sudden changes in flow direction actively reorient and randomize the velocity vectors, thus, ensuring turbulence throughout the bloodstream. During turbulent flow, the velocity vectors of the blood become more random and, in some cases, become perpendicular to the axis of the artery. In addition, as the velocity of the blood within the artery decreases and reverses direction during the cardiac cycle, additional turbulence is induced and turbulent motion is sustained throughout the duration of each pulse through the same mechanisms described above.

Thus, a large portion of the volume of warm blood in the vessel is actively brought in contact with the heat transfer element 14, where it can be cooled by direct contact, rather than being cooled largely by conduction through adjacent laminar layers of blood. As noted above, the depth of the grooves 26,30,34 is greater than the depth of the boundary layer which would develop if a straight-walled heat transfer element were introduced into the blood stream. In this way, free stream turbulence is induced. In the preferred embodiment, in order to create the desired level of turbulence in the entire blood stream during the whole cardiac cycle, the heat transfer element 14 creates a turbulence intensity greater than 0.05. The turbulence intensity may be greater than 0.055,0.06, 0.07 or up to 0.10 or 0.20 or greater. If the heat transfer element according to the invention were placed in a pipe approximately the same size as an artery carrying a fluid having a similar velocity, density and viscosity of blood and having a constant (rather than pulsatile) flow, Reynolds numbers of greater than 1,900, 2,000, 2,100, 2,200 or even as much as 2,300, 2,400 or 2,600 or greater would be developed. Further, the design shown in FIGS. 4, 5, 6 and 7 provides a similar mixing action for the working fluid inside the heat transfer element 14.

The heat transfer element 14 has been designed to address all of the design criteria discussed above. First, the heat transfer element 14 is flexible and is made of highly conductive material. The flexibility is provided by a segmental distribution of bellows sections 21,25 which provide an articulating mechanism. Bellows have a known convoluted design which provides flexibility. Second, the exterior surface area 37 has been increased through the use of helical ridges 28,32,36 and helical grooves 26,30,34. The ridges also allow the heat transfer element 14 to maintain a relatively atraumatic profile, thereby minimizing the possibility of damage to the vessel wall. Third, the heat transfer element 14 has been designed to promote turbulent kinetic energy both internally and externally. The segment design allows the direction of the grooves to be reversed between segments. The alternating helical rotations create an alternating flow that results in mixing the blood in a manner analogous to the mixing action created by the rotor of a washing machine that switches directions back and forth. This mixing action is intended to promote high level turbulent kinetic energy to enhance the heat transfer rate. The alternating helical design also causes beneficial mixing, or turbulent kinetic energy, of the working fluid flowing internally.

Figure 8:
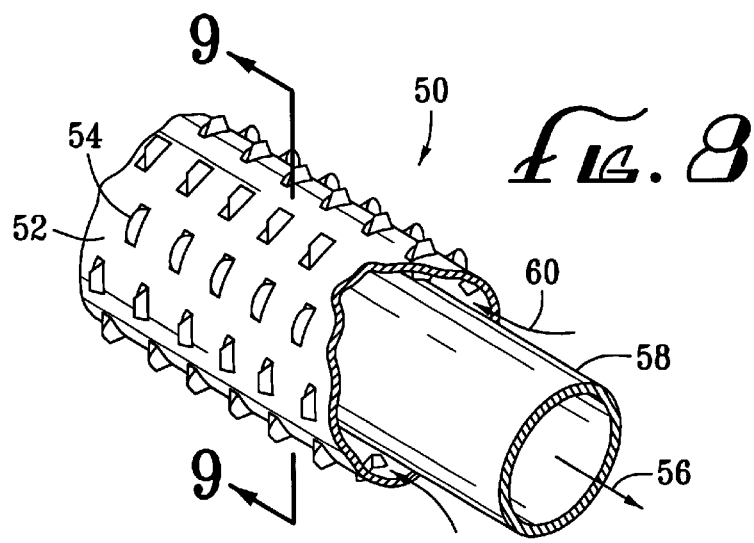
FIG. 8 is a cut-away perspective view of an alternative embodiment of a heat transfer element according to the invention.

FIG. 8 is a cut-away perspective view of an alternative embodiment of a heat transfer element 50. An external surface 52 of the heat transfer element 50 is covered with a series of axially staggered, circumferentially overlapping protrusions 54. The staggered, overlapping nature of the protrusions 54 is readily seen with reference to FIG. 9 which is a transverse cross-sectional view taken along the line 9—9 in FIG. 8. In order to induce free stream turbulence, the height, $d_p$, of the staggered protrusions 54 is greater than the thickness of the boundary layer which would develop if a smooth heat transfer element had been introduced into the blood stream. As the blood flows along the external surface 52, it collides with one of the staggered protrusions 54 and turbulent flow is created. As the blood divides and swirls along side of the first staggered protrusion 54, it collides with another staggered protrusion 54 within its path preventing the re-lamination of the flow and creating yet more turbulence. In this way, the velocity vectors are randomized and free stream turbulence is created. As is the case with the preferred embodiment, this geometry also induces a turbulent effect on the internal coolant flow.

A working fluid is circulated up through an inner coaxial lumen 56 defined by an insulating coaxial tube 58 to a distal tip of the heat transfer element 50. The working fluid then traverses an outer coaxial lumen 60 in order to transfer heat to the exterior surface 52 of the heat transfer element 50. The inside surface of the heat transfer element 50 is similar to the exterior surface 52, in order to induce turbulent flow of the working fluid.

Figure 9:
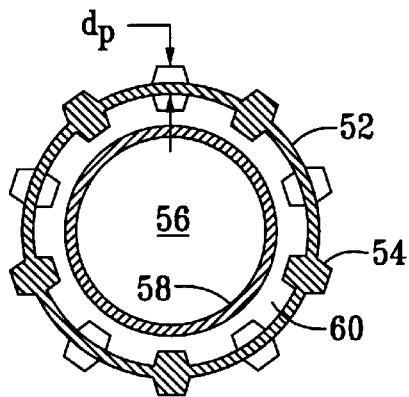
FIG. 9 is a transverse section view of the heat transfer element of FIG. 8.

In an alternative embodiment of the invention, one or more of the segments 20, 22, 24, described with respect to FIGS. 4–7, may be replaced with a segment having overlapping protrusions 54, such as those described with respect to FIGS. 8–9.

With reference to FIGS. 10–14, numerous embodiments of a heat transfer mechanism for selective heating or cooling of an organ will now be described. The heat transfer mechanism discussed with respect to FIGS. 10–14 is similar to the heat transfer element described with reference to FIGS. 4 and 8 above, but further includes a turbulence-enhancing element for enhancing the turbulent kinetic energy in the free stream and boundary layer of the heat transfer element 14. It will be shown that the turbulence-enhancing element may enhance turbulence around the heat transfer element 14 in numerous ways such as, but not by way of limitation, increasing the velocity of the blood contacting the heat transfer element 14, altering the normal direction of blood flow contacting the heat transfer element 14, and by increasing the level of turbulence in the blood flow before the blood reaches the heat transfer element 14, i.e., creating "pre-turbulence."

Figure 10:
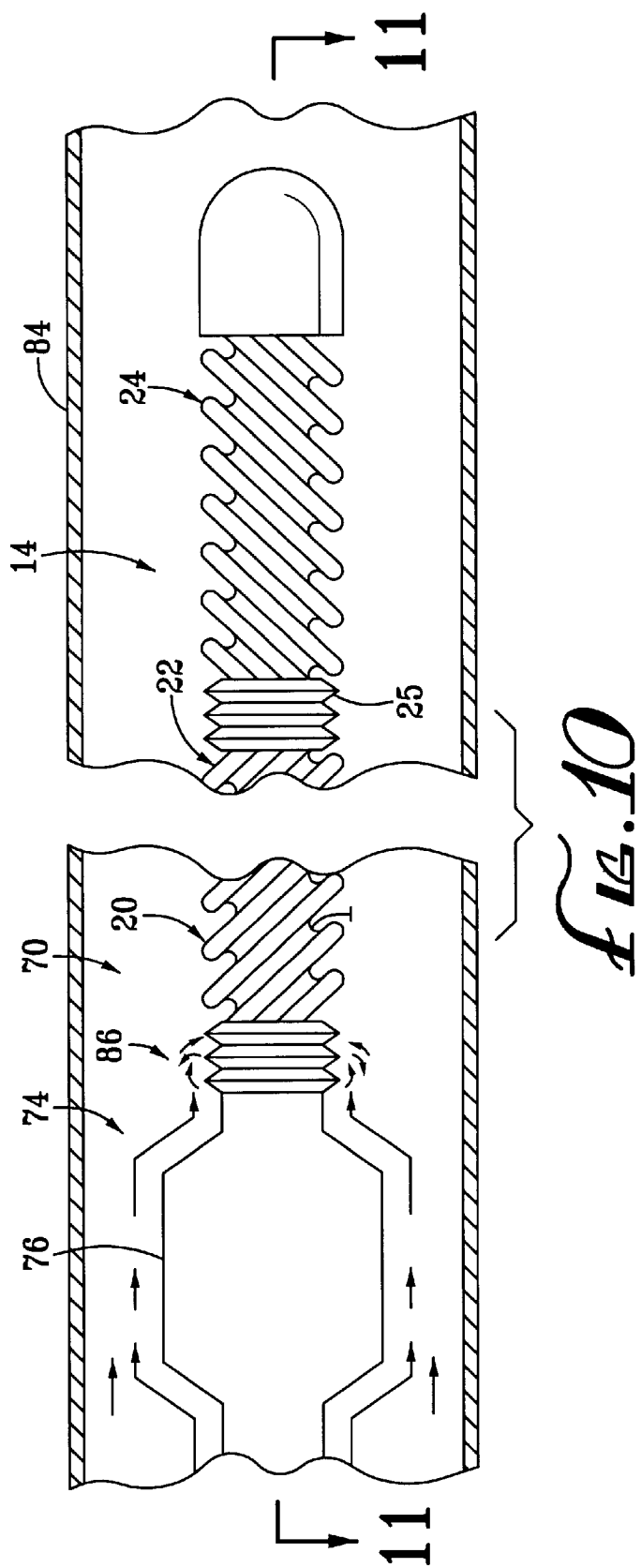
FIG. 10 is an elevation view of an embodiment of a heat transfer mechanism according to the invention in use within a blood vessel.
Figure 11:
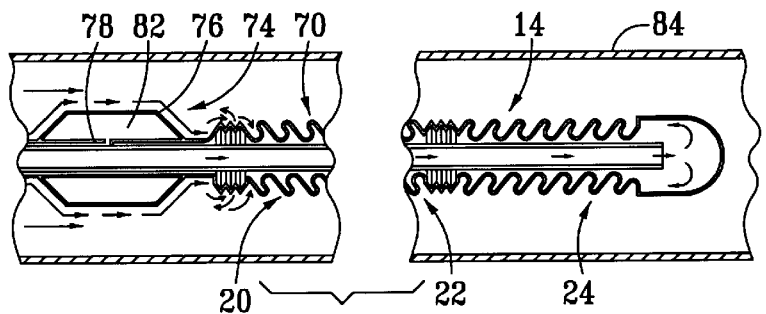
FIG. 11 is a longitudinal cross-sectional view of the heat transfer mechanism illustrated in FIG. 10.

With reference to FIGS. 10 and 11, a heat transfer mechanism 70 constructed in accordance with an embodiment of the invention will now be described. The heat transfer mechanism 70 is located at a distal portion of a supply catheter 12. The heat transfer mechanism 70 includes a heat transfer element 14 located distally of a turbulence-enhancing element 74. The heat transfer element 14 may be the same as that described above with respect to FIGS. 4–7 and, thus, will not be described in any further detail. While for purposes of brevity the discussion herein is directed to a heat transfer element 14, it will be readily apparent to those skilled in the art that a heat transfer element other than that described with respect to FIGS. 4–7 may be used. For example, the heat transfer element 50 described with respect to FIGS. 8–9 may be used. In the embodiment shown in FIGS. 10 and 11, the turbulence-enhancing element 74 is an expandable micro-balloon 76. A lumen 78 (FIG. 11) is located within the supply catheter 12 for expanding and contracting the micro-balloon 76 with a fluid, such as air. Although the micro-balloon 76 is described as being expanded and contracted using air, it will be readily apparent to those skilled in the art that other fluids, such as saline, may be used. The lumen 78 is in communication with a fluid source at a proximal end of the lumen 78 and in communication with an interior 82 of the micro-balloon 76 at a distal end. In an alternative embodiment of the invention, the catheter 12 may include more than one lumen for expanding the micro-balloon 76. A conventional control mechanism may be connected to the proximal end of the lumen 78 for controlling expansion and contraction of the micro-balloon 76. Examples of control mechanisms include, but not by way of limitation, a plunger, a squeezable bladder, or a pump.

The heat transfer mechanism 70 will now be generally described in use. The heat transfer mechanism 70 is positioned in a desired location in a patient's blood vessel 84, upstream from the desired organ to be cooled. During positioning of the heat transfer mechanism 70, the micro-balloon 76 is provided in a deflated or collapsed state to facilitate navigation of the catheter 12 and heat transfer mechanism 70 through the patient's vascular system. Once the heat transfer mechanism 70 is in position within the blood vessel, the micro-balloon 76 is expanded by filling it with fluid. In an expanded state, the micro-balloon 76 restricts the available blood flow volume in that region of the blood vessel and thus causes the blood adjacent the balloon 76 to travel at greater velocity compared to when the balloon 76 is in a collapsed state. However, as this blood passes the micro-balloon 76, the blood flow volume area is again expanded and the blood floods this volume where the heat transfer element 14 is located. Turbulence is enhanced along the heat transfer element, especially at a proximal portion 86 of the heat transfer element 14, by the changing direction of the velocity vectors of the blood flow contacting the segments 20, 22, 24. The blood contacts the successive alternating helical heat transfer segments 20, 22, 24 creating alternating flow that results in mixing the blood. This mixing action promotes high level turbulent kinetic energy to enhance the heat transfer rate between the heat transfer element 14 and the blood. The micro-balloon 76 further promotes or enhances this high level turbulent kinetic energy by increasing the velocity of the blood contacting the heat transfer element 14.

Figure 12:
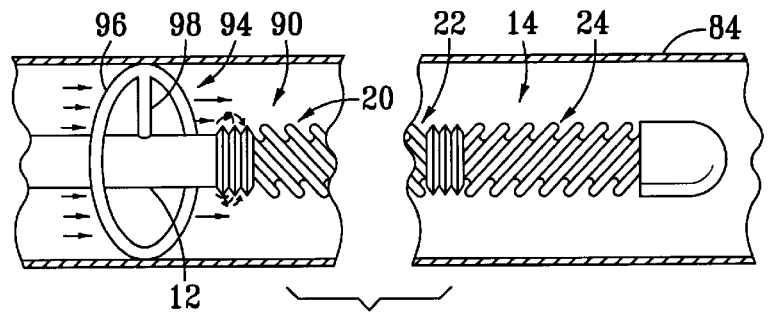
FIG. 12 is an elevation view of an another embodiment of a heat transfer mechanism according to the invention in use within a blood vessel.

With reference to FIG. 12, a heat transfer mechanism 90 constructed in accordance with another embodiment of the invention will now be described. The heat transfer mechanism 90 includes a heat transfer element 14 similar to that described above and a turbulence-enhancing element 94 in the form of an expandable micro-ring balloon 96. An internal lumen similar to the lumen 78 described above with respect to FIG. 11 is located within the catheter 12 and in communication with a fluid source and control mechanism at a proximal end for controlling inflation and deflation of the micro-ring balloon 96. A feed lumen 98 extends radially from the catheter 12 and communicates a distal end of the internal lumen with the micro-ring balloon 96. The micro-ring balloon 96 functions in a similar manner to the micro-balloon 76 described above with respect to FIG. 10, except the micro-ring balloon 96 cause blood to flow away from the blood vessel wall and into the heat transfer element 14, inducing additional turbulence. Although the micro-ring balloon 96 is shown in communication with a single lumen 98, it will be readily apparent to those skilled in the art that in an alternative embodiment, the balloon 96 may be in communication with multiple lumens. Multiple lumens provide the micro-ring balloon 96 with additional support and facilitate expansion and contraction of the micro-ring balloon 96 with the vessel 84.

Figure 13:
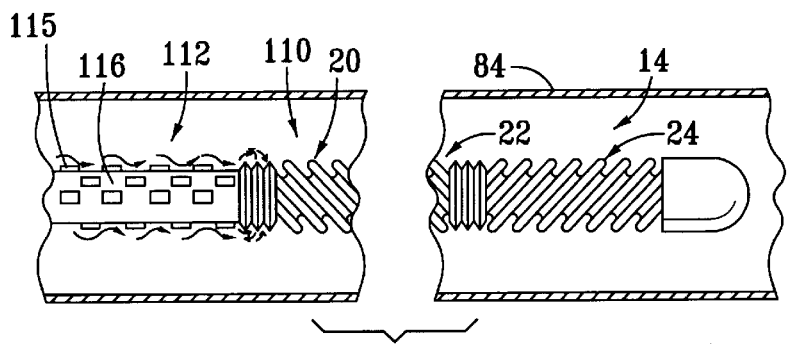
FIG. 13 is an elevation view of an additional embodiment of a heat transfer mechanism according to the invention in use within a blood vessel.

With reference to FIG. 13, a heat transfer mechanism 110 constructed in accordance with a further embodiment of the invention will be described. The heat transfer mechanism 110 includes a heat transfer element 14 similar to that described above and a turbulence-enhancing element 112 in the form of axially staggered and circumferentially overlapping protrusions 115 located on an external surface 116 of the catheter 12. The protrusions 115 may be similar to the protrusions 54 described above with respect to FIGS. 8 and 9, except they are preferably located proximal of the heat transfer element 14 instead of on the heat transfer element 14. As the blood flows along the external surface 116, it collides with the staggered protrusions 115 and turbulent flow, i.e., "pre-turbulence" is initiated. As the blood divides and swirls around a staggered protrusion 115, it collides with another staggered protrusion 115 within its path, preventing the re-lamination of the flow and creating additional turbulence. The turbulent blood then contacts the successive alternating helical heat transfer segments 20–24, creating alternating flow that results in additional mixing of the blood. This mixing action promotes further high level turbulent kinetic energy to enhance the heat transfer rate between the heat transfer element 14 and the blood.

Figure 14:
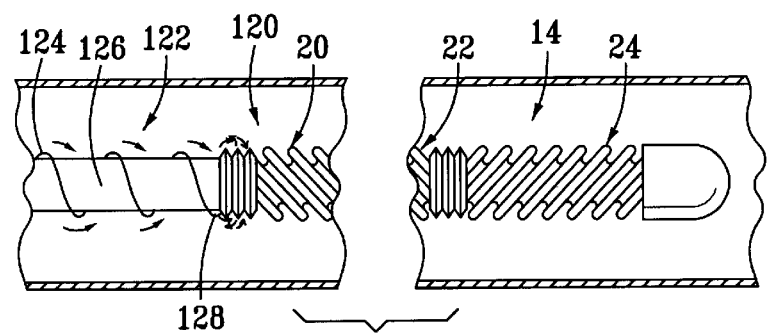
FIG. 14 is an elevation view of a further embodiment of a heat transfer mechanism according to the invention in use within a blood vessel.

With reference to FIG. 14, a heat transfer mechanism 120 constructed in accordance with a further embodiment of the invention will be described. The heat transfer mechanism 120 includes a heat transfer element 14 similar to that described above and a turbulence-enhancing element 122 in the form of a temperature sensor wire 124 such as thermocouple wire helically wound around an external surface 126 of the catheter 12. The temperature sensor wire 124 may include a shrink wrap to hold the wire 124 in place. The temperature sensor wire 124 includes a temperature sensor 128 such as a thermocouple 128 in thermal contact with the heat transfer element 14. In an alternative embodiment, the thermocouple 128 may be a thermistor or similar temperature sensor coupled to a wire for measuring the temperature of the heat transfer element. The thermocouple 128 measures the temperature of the heat transfer element 14 for feedback control of the working fluid temperature. The thermocouple 128 may also be disposed distal of the heat transfer element 14 to measure the temperature of the blood downstream of the heat transfer element 14, e.g., measuring the temperature of the cooled blood. The helically wound thermocouple wire 124 causes blood to swirl over the external surface 126 of the catheter, re-directing the blood flow prior to contact with the heat transfer element 14. The re-direction and swirling of the blood flow further enhances the amount of turbulence created when the blood contacts the successive alternating helical heat transfer segments 20–24. In an alternative embodiment of the invention, a thick wire not used for measuring temperature may replace the thermocouple wire 124 proximal to the heat transfer element. In a further embodiment, a wire, e.g., thermocouple wire or thick wire, may be helically wrapped around a smooth exterior surface of a heat transfer element such as exterior surface 52 described above with respect to FIGS. 8 and 9. The helically wrapped wire would induce turbulent blood flow around the heat transfer element, enhancing heat transfer in this area.

Figure 15:
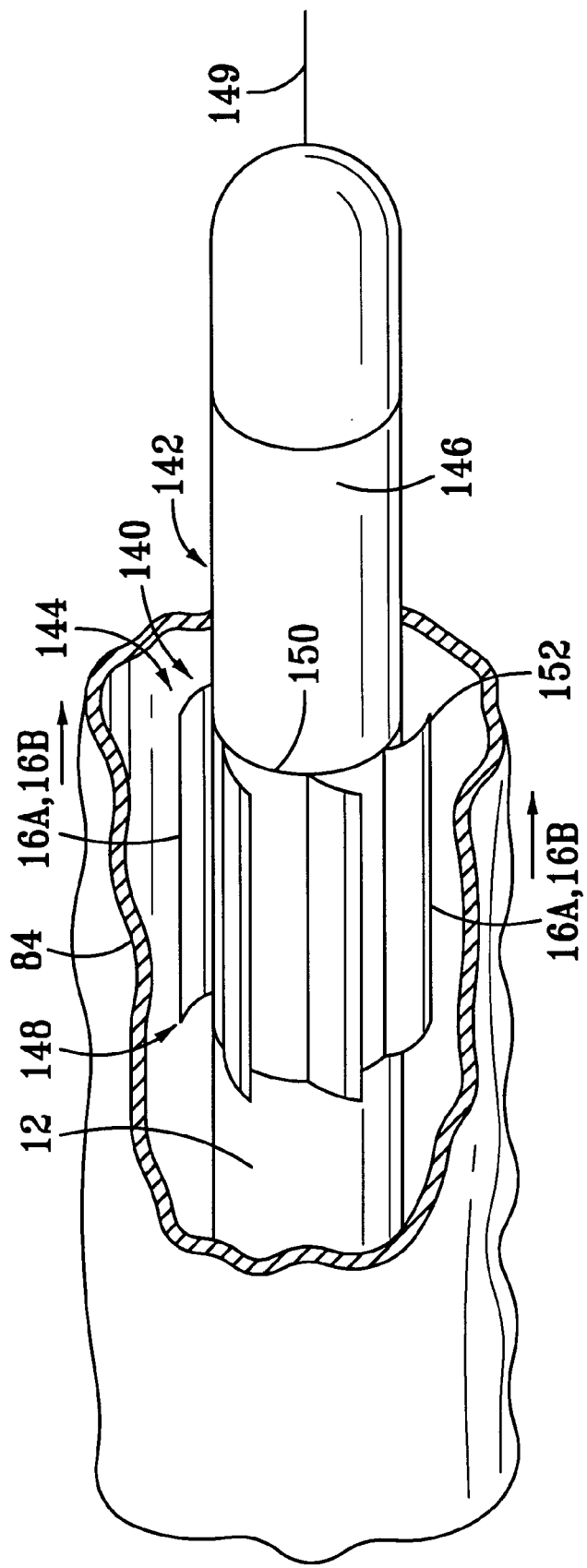
FIG. 15 is a perspective view of a heat transfer mechanism constructed in accordance with a still further embodiment of the invention in use within a blood vessel.

With reference to FIGS. 15, 16A and 16B, a heat transfer mechanism 140 constructed in accordance with an additional embodiment of the invention will be described. The heat transfer mechanism 140 includes a heat transfer element 142 and a turbulence-enhancing element 144. The heat transfer element 142 has a primarily smooth external surface 146 adapted to contact blood within the blood vessel 84. In an alternative embodiment, the heat transfer element 142 has turbulence-inducing features similar to those described above. The turbulence-enhancing element 144 includes a turbulence-generating fan 148. The fan 148 preferably rotates about an axis 149, coaxial with the axis of the catheter 12. The fan 148 includes a rotating hub 150 having multiple blades 152 extending therefrom. The fan 148 is adapted to spin upon influence of blood flow within the vessel 84. The blades 152 are constructed to move away from the hub 150 (FIG. 16B) upon influence of blood flow and towards the hub 150 (FIG. 16A), in a low profile configuration, when blood flow lessens or ceases. A low-profile configuration means that the blades 152 are located close enough to the external surface 146 of the catheter to prevent the fan 148 from catching the vasculature upon introduction and removal of the heat transfer element 142. Referring to FIGS. 16A and 16B, bearings 153 located between the hub 150 and an external portion 154 of the catheter 12 allow the fan 148 to rotate. The hub 150 is appropriately sealed with respect to the catheter 12 in order to prevent contamination of the blood and protect the bearings 152. The rotating fan 148 induces high level turbulent kinetic energy that enhances the heat transfer rate between the smooth heat transfer element 142 and the blood.

With reference to FIG. 17, a heat transfer mechanism 160 constructed in accordance with an additional embodiment of the invention will be described. The heat transfer mechanism includes a heat transfer element 142 similar to that described above with respect to FIG. 15 and a turbulence-enhancing element 162. The turbulence-enhancing element 162 includes a turbulence generating fan 164 similar to fan 148 described above, except the fan 164 includes an internal driving mechanism 166 for rotating the fan 164.

The driving mechanism 166 may include an input lumen 168 and an output lumen 169 in communication with a pump and fluid source at respective proximal ends of the lumens 168, 169 and a fluid drive tunnel 175 at respective distal ends 176, 177 of the lumens 168, 169. The fan 164 includes a rotating hub 170 with multiple blades 172 that move away from the hub 170 upon forced rotation of the fan 164 and towards the hub 170 when the fan 164 ceases rotation. Bearings 174 are located between the hub 170 and the external portion 154 of the catheter 12. The hub 170 is sealed with respect to the catheter 12 in order to prevent contamination of the blood and protect the bearings 174. The fan 164 includes internal blades 178 located within the fluid drive tunnel 175.

Pressurized fluid such as air is pumped through the input lumen 168 and into the fluid drive tunnel 175. Air flows through the fluid drive tunnel 175 in the direction of the arrows, causing the fan 164 to rotate via the internal blades 178. Air exits the fluid drive tunnel 175 through the output lumen 169.

The rotating fan 164 induces high level turbulent kinetic energy that enhances the heat transfer rate between the smooth heat transfer element 142 and the blood. It will be readily appreciated that multiple variations may exist on the heat transfer mechanism 160. For example, in an alternative embodiment, the internal driving mechanism 166 may be constructed so that the working fluid drives the fan 164 via the fluid drive tunnel 175 and internal blades 178. Other mechanical driving mechanisms may be used to drive the fan 164 such as, but not by way of limitation, a motor coupled to a rotatable drive shaft.

Figure 18A:
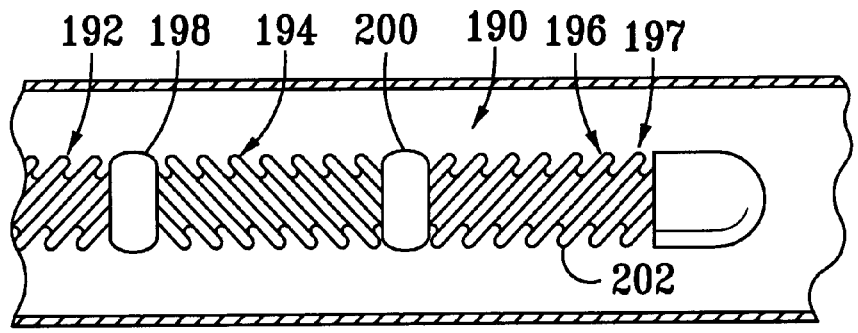
FIGS. 18A, 18B, 18C are elevation views of a further embodiment of a heat transfer mechanism according to the invention in use within a blood vessel during various states of operation.
Figure 18B:
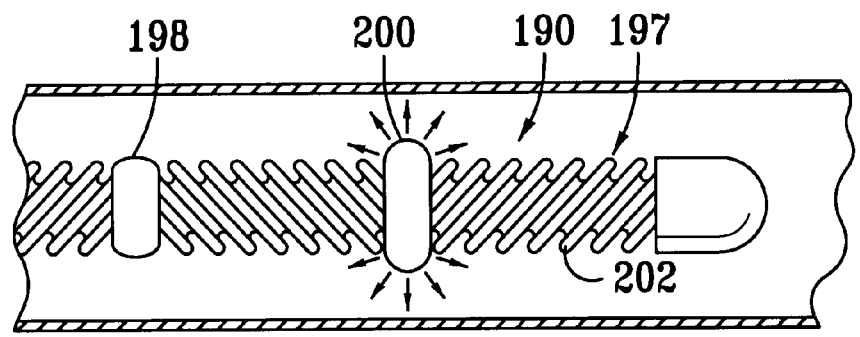
Figure 18C:
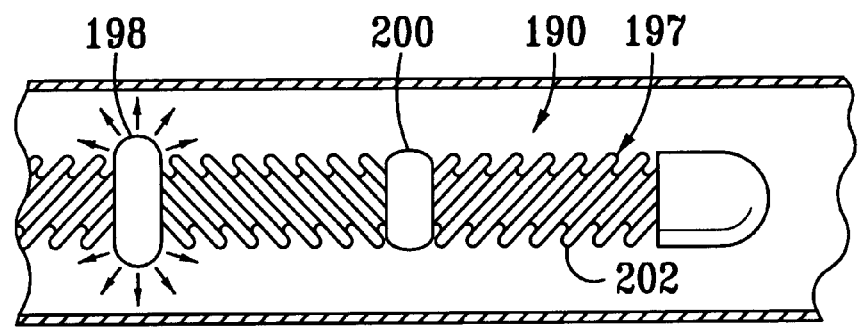

With reference to FIGS. 18A–18C, a heat transfer mechanism 190 constructed in accordance with an additional embodiment of the invention will be described. The heat transfer mechanism 190 includes a series of elongated, articulated heat transfer segments 192, 194, 196, which are similar to the segments 20, 22, 24 discussed above with respect to FIGS. 4–7, connected by flexible joints in the form of tubing sections 198, 200. The heat transfer segments 192, 194, 196 serve as a heat transfer element 197 for transferring heat between the blood flow and the heat transfer element 197. The tubing sections 198, 200 are made of a flexible biocompatible material such as a polymer that is seamless and nonporous. The tubing sections 198, 200 are adapted to bend, extend and compress, which increases the flexibility of the heat transfer element 197 so that it is more readily able to navigate through blood vessels. The tubing sections 198, 200 also provide axial compression of the heat transfer element 197, which can limit the trauma when the distal end of the heat transfer element 197 abuts a blood vessel wall. The tubing sections 198, 200 are also able to tolerate cryogenic temperatures without a loss of performance. During use of the heat transfer mechanism 190, working fluid is pulsed through an inner coaxial lumen of an inner tube and out of a distal end of the inner tube into an outer lumen (See, for example, FIG. 5, inner coaxial lumen 40, inner tube 42, outer lumen 46). As the working fluid is pulsed through the outer lumen, heat is transferred from the working fluid to an exterior surface 202 of the heat transfer element 197. As the working fluid is pulsed through the inner lumen and outer lumen, the flexible tubing sections 198, 200, which include an internal area in fluid communication with the outer lumen, sequentially pulsate or expand, as shown in FIGS. 18B and 18C. The pulsating bellow sections 198, 200 transfer their vibrations to the blood flow, promoting turbulent kinetic energy as the blood flow contacts the heat transfer element 197. In addition, the expanded diameter of the flexible bellow sections 198, 200 caused by each pulsation promotes high level turbulent kinetic energy by increasing the velocity of the blood contacting the heat transfer element 197 in a manner similar to that described above for the micro-balloon 76.

In an alternative embodiment of the invention, the tubing sections 199, 200 may be replaced with micro-balloons, which are connected to separate lumens for individually controlling the pulsation of the balloon sections.

Figure 19:
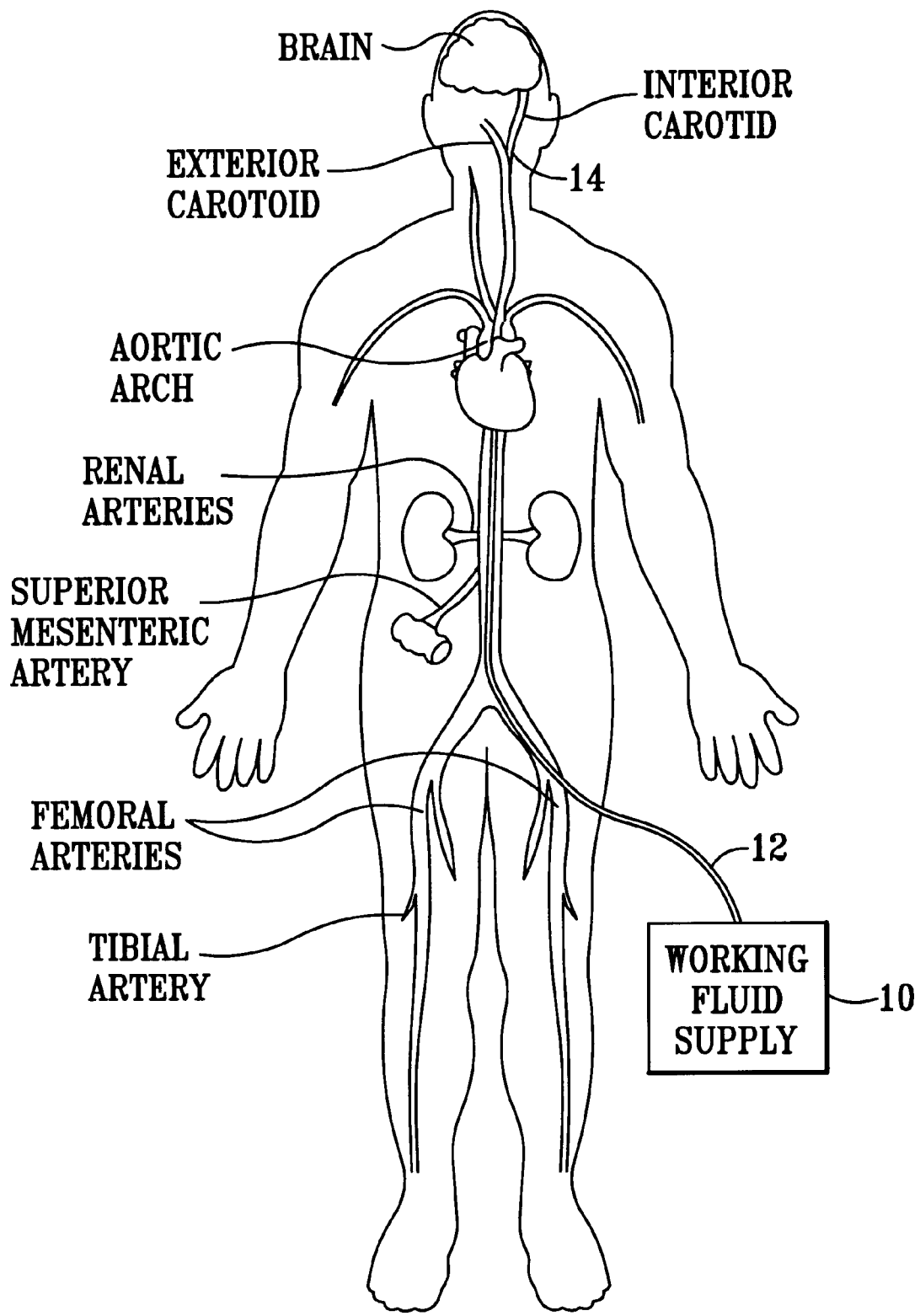
FIG. 19 is a schematic representation of an embodiment of the invention being used to cool the brain of a patient.

FIG. 19 is a schematic representation of the invention being used to cool the brain of a patient. The selective organ hypothermia apparatus shown in FIG. 19 includes a working fluid supply 10, preferably supplying a chilled liquid such as water, alcohol or a halogenated hydrocarbon, a supply catheter 12 and the heat transfer element 14. The working fluid supply 10 preferably supplies fluid via a pump (not shown). The supply catheter 12 has a coaxial construction. An inner coaxial lumen within the supply catheter 12 receives coolant from the working fluid supply 10. The coolant travels the length of the supply catheter 12 to the heat transfer element 14 which serves as the cooling tip of the catheter. At the distal end of the heat transfer element 14, the coolant exits the insulated interior lumen and traverses the length of the heat transfer element 14 in order to decrease the temperature of the heat transfer element 14. The coolant then traverses an outer lumen of the supply catheter 12 so that it may be disposed of or recirculated. The supply catheter 12 is a flexible catheter having a diameter sufficiently small to allow its distal end to be inserted percutaneously into an accessible artery such as the femoral artery of a patient as shown in FIG. 19. The supply catheter 12 is sufficiently long to allow the heat transfer element 14 at the distal end of the supply catheter 12 to be passed through the vascular system of the patient and placed in the internal carotid artery or other small artery. The method of inserting the catheter into the patient and routing the heat transfer element 14 into a selected artery is well known in the art.

Although the working fluid supply 10 is shown as an exemplary cooling device, other devices and working fluids may be used. For example, in order to provide cooling, freon, perflourocarbon or saline may be used.

The heat transfer element of the present invention can absorb or provide over 75 Watts of heat to the blood stream and may absorb or provide as much a 100 Watts, 150 Watts, 170 Watts or more. For example, a heat transfer element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

The practice of the present invention is illustrated in the following non-limiting example.

Exemplary Procedure

1. The patient is initially assessed, resuscitated, and stabilized.
2. The procedure is carried out in an angiography suite or surgical suite equipped with fluoroscopy.
3. Because the catheter is placed into the common carotid artery, it is important to determine the presence of stenotic atheromatous lesions. A carotid duplex (doppler/ultrasound) scan can quickly and non-invasively make this determinations. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities >100 cm/sec in the internal indicate the presence of at least 70% stenosis. Stenosis of 70% or more may warrant the placement of a stent to open up the internal artery diameter.

4. The ultrasound can also be used to determine the vessel diameter and the blood flow and the catheter with the appropriately sized heat transfer element could be selected.
5. After assessment of the arteries, the patients inguinal region is sterilely prepped and infiltrated with lidocaine.
6. The femoral artery is cannulated and a guide wire may be inserted to the desired carotid artery. Placement of the guide wire is confirmed with fluoroscopy.
7. An angiographic catheter can be fed over the wire and contrast media injected into the artery to further to assess the anatomy of the carotid.
8. Alternatively, the femoral artery is cannulated and a 10–12.5 french (f) introducer sheath is placed.
9. A guide catheter is placed into the desired common carotid artery. If a guiding catheter is placed, it can be used to deliver contrast media directly to further assess carotid anatomy.
10. A 10 f–12 f (3.3–4.0 mm) (approximate) cooling catheter is subsequently filled with saline and all air bubbles are removed.
11. The cooling catheter is placed into the carotid artery via the guiding catheter or over the guidewire. Placement is confirmed with fluoroscopy.
12. Alternatively, the cooling catheter tip is shaped (angled or curved approximately 45 degrees), and the cooling catheter shaft has sufficient pushability and torqueability to be placed in the carotid without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 0° C.
14. Cooling is initiated by starting the pump mechanism. The saline within the cooling catheter is circulated at 5 cc/sec. The saline travels through the heat exchanger in the chilled water bath and is cooled to approximately 1° C.
15. It subsequently enters the cooling catheter where it is delivered to the heat transfer element. The saline is warmed to approximately 5–7° C. as it travels along the inner lumen of the catheter shaft to the end of the heat transfer element.
16. The saline then flows back through the heat transfer element in contact with the inner metallic surface. The saline is further warmed in the heat transfer element to 12–15° C., and in the process, heat is absorbed from the blood cooling the blood to 30° C. to 32° C.
17. The chilled blood then goes on to chill the brain. It is estimated that 15–30 minutes will be required to cool the brain to 30 to 32° C.
18. The warmed saline travels back to down the outer lumen of the catheter shaft and back to the chilled water bath were it is cooled to 1° C.
19. The pressure drops along the length of the circuit are estimated to be 2–3 atmospheres.
20. The cooling can be adjusted by increasing or decreasing the flow rate of the saline. Monitoring of the temperature drop of the saline along the heat transfer element will allow the flow to be adjusted to maintain the desired cooling effect.
21. The catheter is left in place to provide cooling for 12 to 24 hours.
22. If desired, warm saline can be circulated to promote warming of the brain at the end of the therapeutic cooling period.

While the particular invention as herein shown and disclosed in detail is fully capable of obtaining the objects and providing the advantages stated, it is to be understood that this disclosure is merely illustrative of the presently preferred embodiments of the invention and that no limitations are intended other than as described in the appended claims.

We claim:

1. A heat transfer device for transferring heat to or from surrounding blood flow to heat or cool the surrounding blood flow, comprising:

a catheter capable of insertion into a selected blood vessel in the vascular system of a patient;

a heat transfer element attached to a distal portion of said catheter and adapted to transfer heat to or from surrounding blood flow to heat or cool the surrounding blood flow, the heat transfer device including more than one heat transfer segment forming a blood mixing-enhancing element adapted to enhance mixing of blood flow along said heat transfer element, the blood mixing-enhancing element including a plurality of exterior surface irregularities, said surface irregularities comprise a helical ridge and a helical groove formed on each said heat transfer segment, and said helical ridge and helical groove on each said heat transfer segment has an opposite helical twist to said helical ridge and helical groove on an adjacent heat transfer segment so as to create repetitively changing directions of blood flow in surrounding blood.

2. A heat transfer device for transferring heat to or from surrounding blood flow to heat or cool the surrounding blood flow, comprising:

a catheter capable of insertion into a selected blood vessel in the vascular system of a patient;

a heat transfer element attached to a distal portion of said catheter and adapted to transfer heat to or from surrounding blood flow to heat or cool the surrounding blood flow; and a blood mixing-enhancing element attached to a distal portion of said catheter and adapted to enhance mixing of blood flow along said heat transfer element, said blood mixing-enhancing element located proximal of said heat transfer element.

3. The device of claim 2, wherein said blood mixing-enhancing element includes an expandable micro-balloon.

4. The device of claim 2, wherein said blood mixing-enhancing element includes an expandable micro-ring balloon.

5. The device of claim 2, wherein said blood mixing-enhancing element includes multiple axially staggered and circumferentially overlapping protrusions located along an exterior surface.

6. A heat transfer device for transferring heat to or from surrounding blood flow to heat or cool the surrounding blood flow, comprising:

a catheter capable of insertion into a selected blood vessel in the vascular system of a patient;

a heat transfer element attached to a distal portion of said catheter and adapted to transfer heat to or from surrounding blood flow to heat or cool the surrounding blood flow;

a blood mixing-enhancing element attached to a distal portion of said catheter and adapted to enhance mixing of blood flow along said heat transfer element, said blood mixing-enhancing element located proximal of said heat transfer element and including a temperature sensor wire helically wound around an exterior surface and having a temperature sensor in thermal contact with said heat transfer element for feedback control of said heat transfer element.

7. The device of claim 6, wherein said temperature sensor is a member from the group consisting of thermocouple and thermistor.

8. A heat transfer device for transferring heat to or from surrounding blood flow to heat or cool the surrounding blood flow, comprising:

a catheter capable of insertion into a selected blood vessel in the vascular system of a patient;

a heat transfer element attached to a distal portion of said catheter and adapted to transfer heat to or from surrounding blood flow to heat or cool the surrounding blood flow;

a blood mixing-enhancing element located proximal of said heat transfer element and attached to a distal portion of said catheter and adapted to enhance mixing of blood flow along said heat transfer element; and wherein said catheter includes a longitudinal axis and said blood mixing-enhancing element includes a fan adapted to rotate about an axis coaxial with said longitudinal axis of said catheter.

9. The device of claim 8, wherein said fan is adapted to rotate upon fluid flow past the fan.

10. The device of claim 8, further including a driving mechanism adapted to rotate said fan.

11. The device of claim 8, wherein said fan includes multiple blades adapted to have a low profile when said fan is at rest and expand when in motion.

12. A method for selectively controlling the temperature of blood flow, said method comprising:

providing a catheter having a heat transfer element and a blood mixing-enhancing element attached to a distal portion thereof, the blood mixing-enhancing element located proximal of the heat transfer element;

inserting said catheter through the vascular system of the patient to place said heat transfer element and blood mixing-enhancing element in a desired blood vessel;

creating pre-mixing of blood flow proximal of said heat transfer element with said blood mixing-enhancing element;

circulating fluid into said heat transfer element via an internal lumen of said catheter and via an internal lumen of said heat transfer element;

circulating fluid out of said heat transfer element via an external lumen of said heat transfer element; and transferring heat between said heat transfer element and the blood flow in the blood vessel, whereby said pre-mixing of blood flow proximal of said heat transfer element enhances the transfer of heat between said heat transfer element and blood.

13. A method as recited in claim 12, wherein said blood mixing-enhancing element is an expandable micro-balloon and is located proximal of said heat transfer element, and creating pre-mixing by changing the direction of the velocity vectors of the blood flow contacting said heat transfer element with said expandable micro-balloon.

14. A method as recited in claim 12, wherein said blood mixing-enhancing element is an expandable micro-ring balloon and is located proximal of said heat transfer element, and creating pre-mixing by changing the direction of the velocity vectors of the blood flow contacting said heat transfer element with said expandable micro-ring balloon.

15. A method as recited in claim 12, wherein said blood mixing-enhancing element includes multiple axially staggered and circumferentially overlapping protrusions located along an exterior surface of said catheter proximal to said heat transfer element, and creating pre-mixing by changing the direction of the velocity vectors of the blood flow contacting said heat transfer element with said protrusions.

16. A method as recited in claim 12, wherein said blood mixing-enhancing element is a temperature sensor wire helically wound around said catheter proximal to said heat transfer element, said temperature sensor wire having a temperature sensor in thermal contact with said heat transfer element, and said temperature sensor wire enhances mixing by altering the direction of the blood flow contacting said heat transfer element and by creating pre-mixing of the blood flow prior to contacting said heat transfer element, and said method further including feedback controlling the temperature of the circulating fluid based on the temperature of said heating element.

17. A method for selectively controlling the temperature of blood flow, said method comprising:

providing a catheter having a heat transfer element and a blood mixing-enhancing element attached to a distal portion thereof, said heat transfer element including said blood mixing-enhancing element, said blood mixing-enhancing element including a plurality of segments of helical ridges and grooves having alternating directions of helical rotation;

inserting said catheter through the vascular system of the patient to place said heat transfer element and blood mixing-enhancing element in a desired blood vessel;

creating mixing of blood flow around said heat transfer element by establishing repetitively alternating directions of helical blood flow with said alternating helical rotations of said ridges and grooves;

circulating fluid into said heat transfer element via an internal lumen of said catheter and via an internal lumen of said heat transfer element;

circulating fluid out of said heat transfer element via an external lumen of said heat transfer element; and transferring heat between said heat transfer element and the blood flow in the blood vessel, whereby said mixing of blood flow induced around said heat transfer element enhances the transfer of heat between said heat transfer element and blood.

18. A method for selectively controlling the temperature of blood flow, said method comprising:

providing a catheter having a heat transfer element and a blood mixing-enhancing element attached to a distal portion thereof, said blood mixing-enhancing element including a temperature sensor wire helically wound around said catheter, said temperature sensor wire having a temperature sensor located distal of said heat transfer element;

inserting said catheter through the vascular system of the patient to place said heat transfer element and blood mixing-enhancing element in a desired blood vessel;

creating mixing of blood flow around said heat transfer element with said blood mixing-enhancing element;

circulating fluid into said heat transfer element via an internal lumen of said catheter and via an internal lumen of said heat transfer element;

circulating fluid out of said heat transfer element via an external lumen of said heat transfer element;

transferring heat between said heat transfer element and the blood flow in the blood vessel, whereby said mixing of blood flow induced around said heat transfer element enhances the transfer of heat between said heat transfer element and blood; and feedback controlling the temperature of the circulating fluid based on the temperature of blood downstream of said heating element.

19. A method for selectively controlling the temperature of blood flow, said method comprising:

providing a catheter having a heat transfer element and a blood mixing-enhancing element attached to a distal portion thereof, said blood mixing-enhancing element including a rotating fan;

inserting said catheter through the vascular system of the patient to place said heat transfer element and blood mixing-enhancing element in a desired blood vessel;

creating mixing of blood flow around said heat transfer element with said rotating fan;

circulating fluid into said heat transfer element via an internal lumen of said catheter and via an internal lumen of said heat transfer element;

circulating fluid out of said heat transfer element via an external lumen of said heat transfer element; and transferring heat between said heat transfer element and the blood flow in the blood vessel, whereby said mixing of blood flow induced around said heat transfer element enhances the transfer of heat between said heat transfer element and blood.

20. A heat transfer device for transferring heat to or from surrounding blood flow to heat or cool the surrounding blood flow, comprising:

a catheter for insertion in a blood vessel of a patient;

a heat transfer element attached to a distal end of said catheter and adapted to transfer heat to or from surrounding blood flow to heat or cool the surrounding blood flow;

a plurality of exterior surface irregularities formed on said heat transfer element, said surface irregularities being shaped and arranged to create repetitively changing directions of blood flow in surrounding blood; and a blood mixing-enhancing element associated with said heating element for imparting pre-mixing to blood prior to the blood reaching said heating element.

* * * * *